United States Patent
Hills et al.

(10) Patent No.: US 6,479,994 B1
(45) Date of Patent: *Nov. 12, 2002

(54) INDUSTRIAL ON-LINE ANALYSIS BY NUCLEAR MAGNETIC RESONANCE SPECTROSCOPY

(75) Inventors: Brian Philip Hills, Norwich (GB); Kevin Michael Wright, Norwich (GB)

(73) Assignee: Institute of Food Research, Norwich (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/622,606

(22) PCT Filed: Feb. 12, 1999

(86) PCT No.: PCT/GB99/00447

§ 371 (c)(1),
(2), (4) Date: Sep. 15, 2000

(87) PCT Pub. No.: WO99/42852

PCT Pub. Date: Aug. 26, 1999

(30) Foreign Application Priority Data

Feb. 20, 1998 (GB) .............................. 9803487

(51) Int. Cl.$^7$ ................................ G01V 3/00
(52) U.S. Cl. ................ 324/306; 324/303; 324/318
(58) Field of Search ..................... 324/306, 309, 324/318, 303, 315, 314, 307, 300

(56) References Cited

U.S. PATENT DOCUMENTS

| | | |
|---|---|---|
| 3,693,071 A | 9/1972 | Dolbear |
| 5,363,042 A | 11/1994 | Dumoulin |
| 5,371,464 A | 12/1994 | Rapoport |
| 5,684,399 A * | 11/1997 | Bayer ................ 324/306 |
| 6,268,727 B1 * | 7/2001 | King et al. ............... 324/306 |

FOREIGN PATENT DOCUMENTS

| | | |
|---|---|---|
| EP | 0 726 458 | 8/1996 |
| ZA | 880 732 | 8/1988 |

OTHER PUBLICATIONS

Tellier et al., "On–line Applications in Food Science"; Annual Reports on NMR Spectroscopy, vol. 31, 1995, pp. 105–122.
Car–Brion; "Radio and microwave frequency techniques for online analysis", Transactions of the Institute of Measurement and Control, Jan.–Mar. 1997, UK, vol. 9, No. 1, pp. 3–7.
Colvile; "The laboratory analyser in plant control"; Measurement and Control, Nov. 1984, UK, vol. 17, No., 10, pp. 395–398.
C. I. Nichols, et al.—"Hydrogen Transient Nuclear Magnetic Resonance For Industrial Moisture Sensing" Drying Technology, 9(4), pp. 849–873 (1991).

* cited by examiner

Primary Examiner—Edward Lefkowitz
Assistant Examiner—Tiffany A. Fetzner
(74) Attorney, Agent, or Firm—Dickstein Shapiro Morin & Oshinsky LLP (57) ABSTRACT

A nuclear magnetic resonance spectroscopic technique is applied to objects undergoing translational motion for chemical analysis of objects on a conveyor passing through a detector module. The objects are passed through the detector module at a predetermined velocity V, in which there is provided a spatially uniform, constant magnetic field $B_0$, substantially parallel to the direction of the velocity v and a radio frequency field $B_1$ pulse transverse to the field $B_0$. Selected nuclear magnetic resonance parameters from the objects passing through the detector module are then used to determine chemical composition or changes therein.

26 Claims, 9 Drawing Sheets

INDUSTRIAL ON-LINE ANALYSIS BY NUCLEAR MAGNETIC RESONANCE SPECTROSCOPY

The present invention relates to nuclear magnetic resonance phenomena and in particular to the use thereof in spectroscopic analysis.

The on-line analysis of chemical composition of samples undergoing continuous translational motion, for example through pipes or on conveyors is important throughout the food, chemical and pharmaceutical industries. To date, a number of spectroscopic and physical methods are used for on-line compositional analysis, including near infra-red spectroscopy (NIR), microwave sensors and ultrasonics.

However Nuclear Magnetic Resonance (NMR) has not hitherto been exploited in such an on-line mode on continuously moving objects, despite its well established analytical role in the off-line analytical laboratory. A possible exception to this statement is its use in the on-line analysis of slowly flowing liquids and pastes (C. Tellier and F. Mariette, Online applications in Food Science, Annual Reports on NMR spectroscopy, Vol. 31, 1995, 105–122).

However such applications use conventional NMR methodology and hardware and the fluid velocity is therefore limited by the restricted volume over which the magnetic field and/or radiofrequency field is homogeneous.

Another previous on-line analytical application is in the analysis of powders by NMR (C. I. Nicholls and A. De Los Santos, Hydrogen transient NMR for industrial moisture sensing, Drying Technology, vol 9, 1991, 849–873). But this is based on removing a sample of powder (e.g. with a piston arrangement) for analysis while it is stationary, using conventional NMR methods. There are several reasons for the failure to exploit NMR in a general way for on-line analysis of continuously moving samples.

First, most information is obtained in an NMR spectrum when the spectral peaks arising from different molecular species are well resolved. The spectrum is then easier to interpret and the spectral peak areas, which are related to the number of spins contributing to the peak, can be obtained from each resolved peak by simple integration. This has meant that, in off-line analytical laboratories, it is preferable to work with high (i.e. strong) magnetic fields, since the peak separation increases with increasing field strength. Unfortunately, creating high, spatially uniform magnetic fields (eg. above proton resonance frequencies of 100 MHz) requires the use of superconducting magnets. These magnets are very expensive and require regular filling with liquid nitrogen and liquid helium and are not therefore suitable for routine exploitation and use on the factory floor. If lower magnetic fields are used, such as those available with low-cost, robust, permanent magnets (with proton resonance frequencies less than approximately 20 MHz), the spectral peaks from different molecular species are not usually resolved in the NMR spectrum, making compositional analysis of the spectrum more complicated. This is probably one reason why low field NMR spectra have not yet been exploited for compositional analysis.

Another reason for the slow exploitation of conventional NMR in an on-line mode is the requirement of field homogeneity, both in the main magnetic field, $B_0$ and in the radiofrequency field, $B_1$. Conventional hardware for generating spatially uniform radiofrequency fields based, for example, on Helmholtz coils, saddle coils and birdcage coils creates uniform radiofrequency radiation only over a limited volume. The NMR spectrum of the moving sample must therefore be acquired while the sample resides inside this limited volume. This severely limits the sample velocity and means that most NMR analysis is performed either in a side-line mode where the sample velocity is slowed, or in an off-line mode on stationary samples.

It is an object of the present invention to provide a method of obtaining magnetic resonance spectroscopic data and deriving chemical composition data therefrom.

It is a further object of the present invention to provide an apparatus which can maintain homogeneous $B_0$ and $B_1$ (RF) fields over a sufficient length of travel of an object undergoing translational motion to enable the collection of spectroscopic nuclear magnetic resonance data for determining chemical composition of the object.

According to one aspect, the present invention provides a method of nuclear magnetic resonance spectroscopy comprising the steps of:

conveying an object to be analysed through an NMR module at a predetermined velocity, v;

generating, within the NMR module, a spatially characterised, constant magnetic field $B_0$ substantially parallel to the direction of the velocity, v;

generating, within the NMR module, a radiofrequency field $B_1$ pulse transverse to field $B_0$;

detecting nuclear magnetic resonance signals weighted with at least one selected nuclear magnetic resonance parameter from said object;

generating a chemical shift resolved spectrum of the conveyed object within the NMR module.

According to a further aspect, the present invention provides apparatus for gathering spectroscopic nuclear magnetic resonance data comprising:

a first field generating means for generating a spatially characterised, constant magnetic field $B_0$ in an NMR module volume having a predetermined length along a longitudinal axis thereof, the $B_0$ field being parallel to said longitudinal axis;

a second field generating means for generating, within the NMR module volume, radiofrequency field $B_1$ pulses transverse to field $B_0$;

receiver means for detecting nuclear magnetic resonance signals weighted with at least one selected nuclear magnetic resonance parameter from said object;

means for generating a chemical shift resolved spectrum of the conveyed object within the NMR module;

wherein at least said second field generating means comprises a coil having cylindrical geometry.

Embodiments of the present invention will now be described, by way of example, and with reference to the accompanying drawings in which.

A design of radiofrequency coil which permits the creation of uniform radiofrequency fields over extended volumes permits NMR to be carried out over much larger spatial volumes, and in particular over an extended length of a pathway of an object undergoing translational motion. This enables it to be used for on-line NMR compositional analysis.

This specification describes the development of a low-cost, robust, and fast, on-line nuclear magnetic resonance (NMR) spectrometer (and associated protocols) suitable for acquiring low-field, poorly resolved NMR spectra of solid (ie. non-fluid) samples undergoing continuous translational motion, although the apparatus can also be used for the analysis of semi-solid, fluid or powder samples similarly undergoing continuous translational motion. It also shows that, like NIR, a well-resolved NMR spectrum is not an essential requirement for compositional analysis so that low cost, robust, low-field permanent magnets (or electromagnets) can be used. Moreover, it exploits a new modified RF coil, together with a cylindrical-shaped low cost magnet, to extend the volume over which the field is spatially uniform thereby eliminating a major restriction on sample velocity.

Let us assume an object to be analysed is travelling with an instantaneous velocity, v(t), which need not be constant. Then, in the minimum time it takes to acquire an NMR signal, AQ (acquisition time), it travels a distance of at least $L_{min}$ given by the integral, $$L_{min} = \int_0^{AQ} dt\, v(t)$$

This means that, for conventional NMR to be successful, the magnetic field, $B_0$ and the radiofrequency field, $B_1$, are preferably both spatially homogeneous over a distance of at least $L_{min}$. This severely limits the range of velocities and acquisition times that can be used with conventional NMR protocols. The unique geometric feature of the apparatus of the present invention as described below, for generating the $B_0$, and radiofrequency field, $B_1$, is that they are both cylinders whose length can be extended indefinitely, at least in principle. They can therefore create spatially homogeneous $B_0$ and $B_1$ fields over any desired length, thereby removing the limitations of previous approaches.

Figure 1:
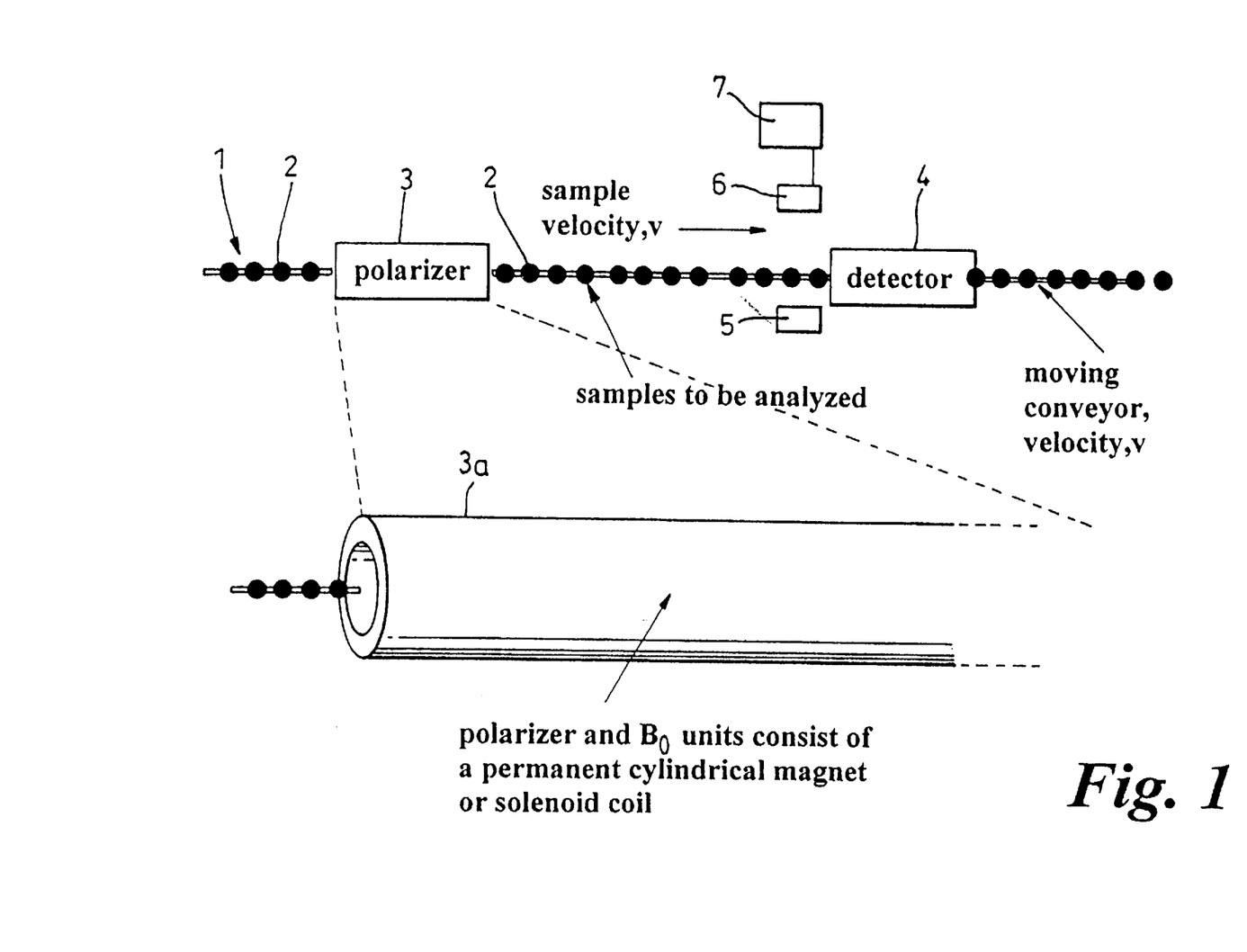
FIG. 1 shows a schematic diagram showing principles of a nuclear magnetic resonance apparatus or module according to the present invention.

We assume that the objects to be analysed are travelling down a conveyor tube, pneumatic tube, belt or other suitable means, schematically shown in FIG. 1 as conveyor 1. The conveyor 1 and all the objects 2 on it preferably move with a constant velocity v.

The hardware required to obtain an NMR spectrum consists of separate cylindrically-shaped units which enclose the conveyor 1 and which can be positioned at various positions along the conveyor. The conveyor carrying the objects then travels down the central axis of the cylindrical units. The modular nature of the hardware ensures greater adaptability to a plurality of applications.

Because the objects to be analysed are travelling with velocity v and it takes a finite time of AQ to acquire the NMR signal(s), it is necessary that the $B_0$ field and radiofrequency field $B_1$ are spatially homogeneous over a distance of at least v×AQ, along the conveyor. According to the preferred embodiment illustrated, the hardware devices as described below for generating the $B_0$ field and radiofrequency field $B_1$ are all cylindrically shaped with lengths that can be extended indefinitely, at least in principle. This distinguishes them from conventional NMR arrangements, such as U-shaped magnets, radiofrequency Helmholtz coils, birdcage coils etc. which would create homogeneous fields only over a limited distance along the conveyor.

The Polarizer Unit

This is illustrated in FIG. 1. We consider an object 2 moving with velocity, v(t). The first step in obtaining an image of the object is to induce longitudinal magnetization within it by application of a constant external magnetic field. This is done in a unit we have called the polarizer 3. If the object has a short $T_1$, then the polarizer 3 consists either of a single, straight, hollow, cylindrical permanent magnet 3a of length L, or a solenoid coil electromagnet 3a of length L. The object moves on a conveyor 1 down the central axis inside the cylindrical polarizer. The time spent inside the polarizer is L/v and for 100% polarization this should be at least $5T_1$. However, 100% polarization is not an essential requirement of the on-line analyser and lower degrees of polarization can be considered. If $T_1$ is long (several seconds), L may be impracticably large, in which case a series of solenoids or permanent magnets can be arranged in, for example, a spiral arrangement and the conveyor passed along the spiral.

Once the object is sufficiently polarized it passes with velocity v into the detector module which creates and detects an NMR signal from the moving object.

The Detector Module

Depending on the application, the detector module 4 consists of two different hardware units. These are called the $B_0$ unit and the RF unit.

The $B_0$ Unit

This is illustrated in FIG. 1. The polarized object 2 emerging from the polarizer 3 on the conveyor 1 passes into a spatially uniform, constant magnetic field, $B_0$ within the detector module 4. Like the polarizer unit 3, the $B_0$ field of the detector module 4 can be created by a hollow cylindrical permanent magnet or by a hollow cylindrical solenoid electromagnet, called, for convenience, the $B_0$ unit.

The conveyor carrying the polarized sample then moves down the middle of the cylinder in a direction parallel to the cylinder axis, and preferably, along the cylinder axis. The direction of the polarized longitudinal magnetization in the sample leaving the polarizer should be in the same direction as $B_0$ in the $B_0$ unit The magnet can be of any desired length provided the $B_0$ field everywhere in the object is spatially uniform. If the object $T_1$ is sufficiently short, then the polarizer and $B_0$ units can be combined into a single continuous unit. This is important for fluid objects to ensure that the magnetization is parallel to $B_0$.

The RF Unit

Figure 2:
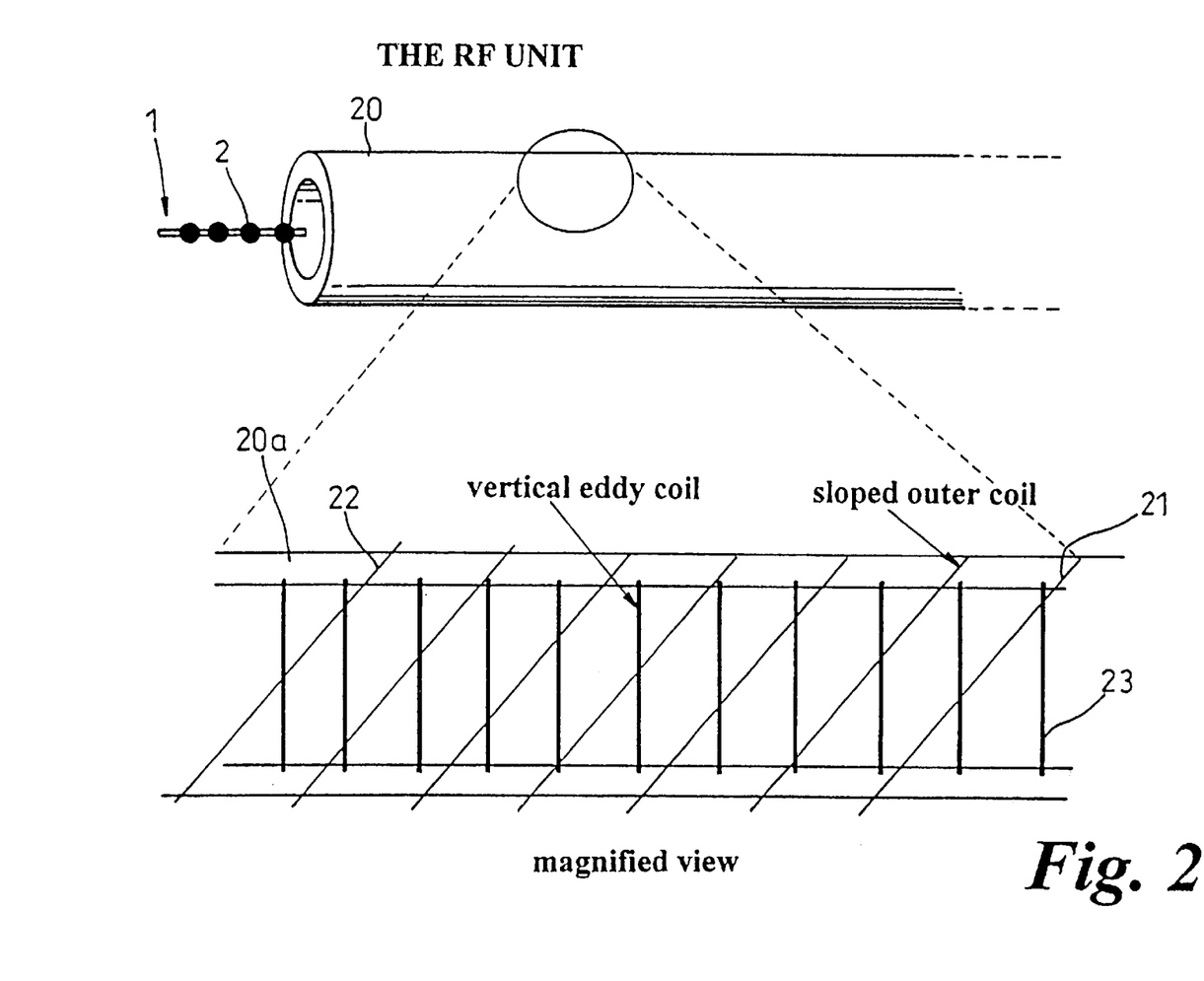
FIG. 2 shows a schematic diagram of an exemplary RF field generating unit suitable for use in the present invention.

This is illustrated in FIG. 2. The on-resonance, radiofrequency field, $B_1$, which must be transverse to $B_0$, can be generated by a specially designed, cylindrical radiofrequency solenoid-like coil which we call the "RF unit". Preferably, this also acts as a receiver coil and is fully described in the reference, "*A solenoid-like coil producing transverse radiofrequency fields for MR imaging*" by E. K. Jeong, D. H. Kim, M. J. Kim, S. H. Lee, J. S. Suh and Y. K. Kwong in *J. Magn. Reson.* 127 (1997) 73–79, Article no. MN971172.

The RF unit 20 as described therein includes a pair of cylindrical coils: a first, outer coil 21 which has the plane of each loop 22 tilted with respect to the cylinder (z) axis to generate an RF field with a component perpendicular to the cylinder axis. A second, inner coil 23 acts as an eddy current coil which eliminates the longitudinal component of the RF field, leaving an RF field entirely perpendicular to the cylinder axis.

A special characteristic of this device is the generation of a uniform radiofrequency field over a long z distance. This distinguishes it from more conventional RF generators such as the standard saddle coil, birdcage or cavity resonator. Such conventional devices could be used for the purposes of the present invention, provided they are of sufficient size that their RF field is uniform over distances exceeding $L_{min}$. The solenoid-like RF unit coil 20a overcomes this limitation and can be easily situated inside and concentric with the $B_0$ unit solenoid coil or permanent magnet. The RF unit 20 is interfaced with conventional electronic equipment and computers for control, acquisition and data processing.

The $G_x$ Unit

Figure 3:
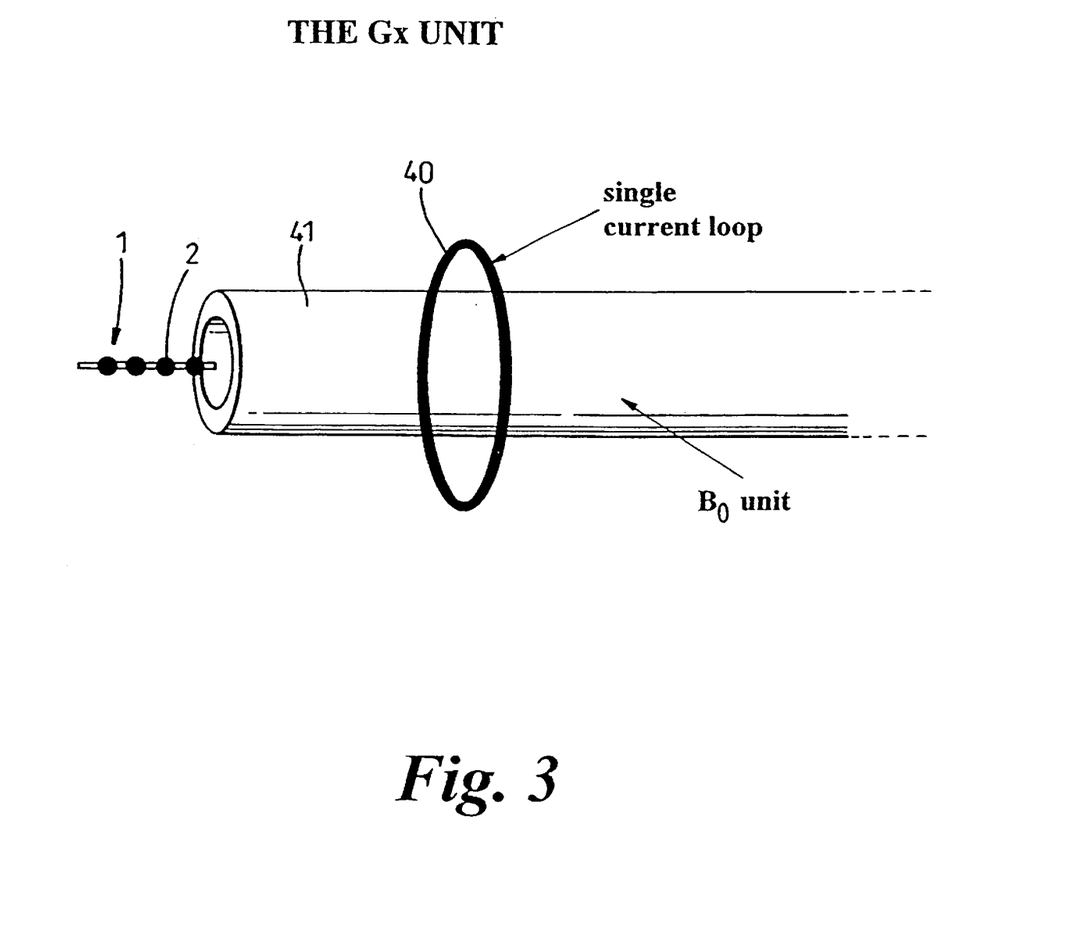
FIG. 3 shows a schematic diagram of an exemplary $G_x$ field generating unit suitable for use in the present invention.

This is illustrated schematically in FIG. 3. Where diffusion-weighted on-line spectroscopy is required, an optional third type of hardware unit comprising a single electric field coil 40 can be used which surrounds the $B_0$ unit 41. The $G_x$ unit creates a steady, spatially localized, non-uniform magnetic gradient $G_x$ transverse to $B_0$. The coil is wound around the gradient of RF solenoid unit at a single location. The magnetic fields generated by the coil 40 are simulated in FIGS. 6 to 9.

Triggering an NMR Pulse Sequence

With further reference to FIG. 1, this can be done electronically by arranging for the object to be analysed to cut a laser or infra-red beam traversing the conveyor 1 as the object 2 enters the detector unit 4. This is provided by suitable conventional light source 5 and a receiver unit 6 coupled to a control circuit 7. An electronic delay can then trigger an appropriate pulse sequence as required by the analysis method being used. If two laser beams are used spaced along the conveyor, the velocity v of the object can also be measured and this used to calculate the timing of radiofrequency pulses automatically.

On-Line Analysis Protocols

A) The Frequency Domain: On-line NMR Spectroscopy

The simple combination of the polarizer, $B_0$ and RF units permits either a free induction decay (FID), spin echo or stimulated echo to be acquired "on-the-fly" from a moving sample. A simple Fourier transform of the FID, spin echo or stimulated echo will therefore create a chemical shift resolved spectrum of the moving sample. At low $B_0$ field strengths and/or with samples having short transverse relaxation times, the spectral resolution may not be sufficient to resolve all the spectral peaks from different chemical constituents in the sample. In this case there are several protocols that can be used to analyse the chemical composition of the moving sample:

1) Calibration Methods

The dependence of the spectral intensity at several frequencies on chemical composition can be used, with multivariate analysis, to determine the composition of the moving object. An analogous procedure is already used commercially in on-line NIR (Near Infra-Red) sensors. Appendix 2 outlines an example methodology.

Figure 4:
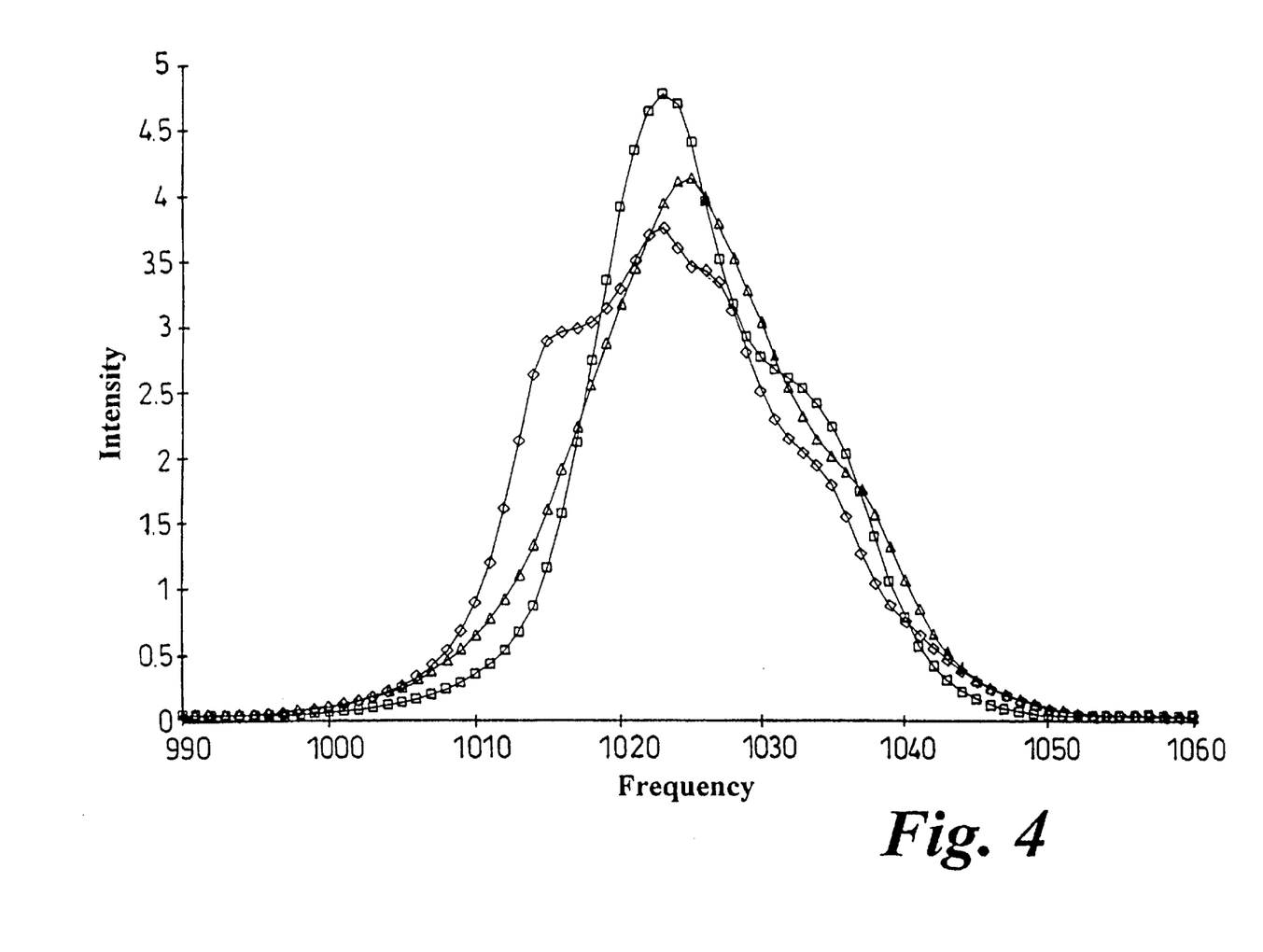
FIG. 4 shows examples of poorly resolved proton spectra for determining chemical composition in accordance with principles of the present invention.

An example of a poorly resolved proton spectrum is shown in FIG. 4. The spectra correspond to three different mousse samples of varying fat and starch content. Separate peaks of fat, water and starch protons are not resolvable, but appear as shoulders in the spectrum. By multivariate analysis of the intensities at three (or more) spectral frequencies (preferably corresponding to the peak maximum of each component) it is possible to create a calibration curve allowing the composition to be deduced from the spectrum.

2) Spectral Weighting Methods

The different chemical constituents in the object can often be distinguished not only by differences in their chemical shifts but also by differences in other intrinsic NMR properties. These NMR properties include, for example the relaxation times $T_2^*$, $T_2$, $T_1$, $T_{ip}$, magnetization transfer rates or the self-diffusion coefficient, D. The following protocols describe how FID's and/or spin echoes or stimulated echoes can be used to create spectra weighted by each of these parameters. The calibration method described above can then be used with the parameter-weighted spectra.

$T_2$ Weighted Spin Echo Spectroscopy $T_2$ weighted spectroscopy can be undertaken using spin echoes created by hard 180° pulses with a standard Hahn-echo or CPMG (Carr Purcell Meiboom Gill) pulse sequence applied to the moving object. $T_2$ weighted spectroscopy is important because different chemical constituents in a food often have difference intrinsic transverse relaxation times. Acquiring spectra with different $T_2$ weighting therefore permits different constituents to be distinguished.

$T_2^*$ Weighting in a Spectrum

In some samples, the signal is attenuated at a faster rate than that caused by simple transverse relaxation ($T_2$). This is caused by local field inhomogeneities and gives rise to relaxation with a time constant, $T_2^*$. An FID created by a single 90° pulse is weighted by the relaxation time $T_2^*$, so that the spectrum obtained by processing the FID will be weighted by $T_2^*$.

$T_1$ Weighting in the Spectrum

There are several possible ways of introducing $T_1$ weighting into the spectra. The simplest is to use the inversion recovery sequence whereby the polarized magnetization, M(0) is inverted by a hard 180° pulse and allowed to recover for a fixed time, $t_1$, adjusted for each application. After the time delay $t_1$, an FID is created by a hard 90° pulse in the RF unit. An alternative pulse sequence which has the advantage of permitting two spectra to be obtained and compared, one with $T_1$ weighting and the other without, involves the stimulated echo pulse sequence.

$T_1$ (low field) Weighting in the Spectrum

Figure 5:
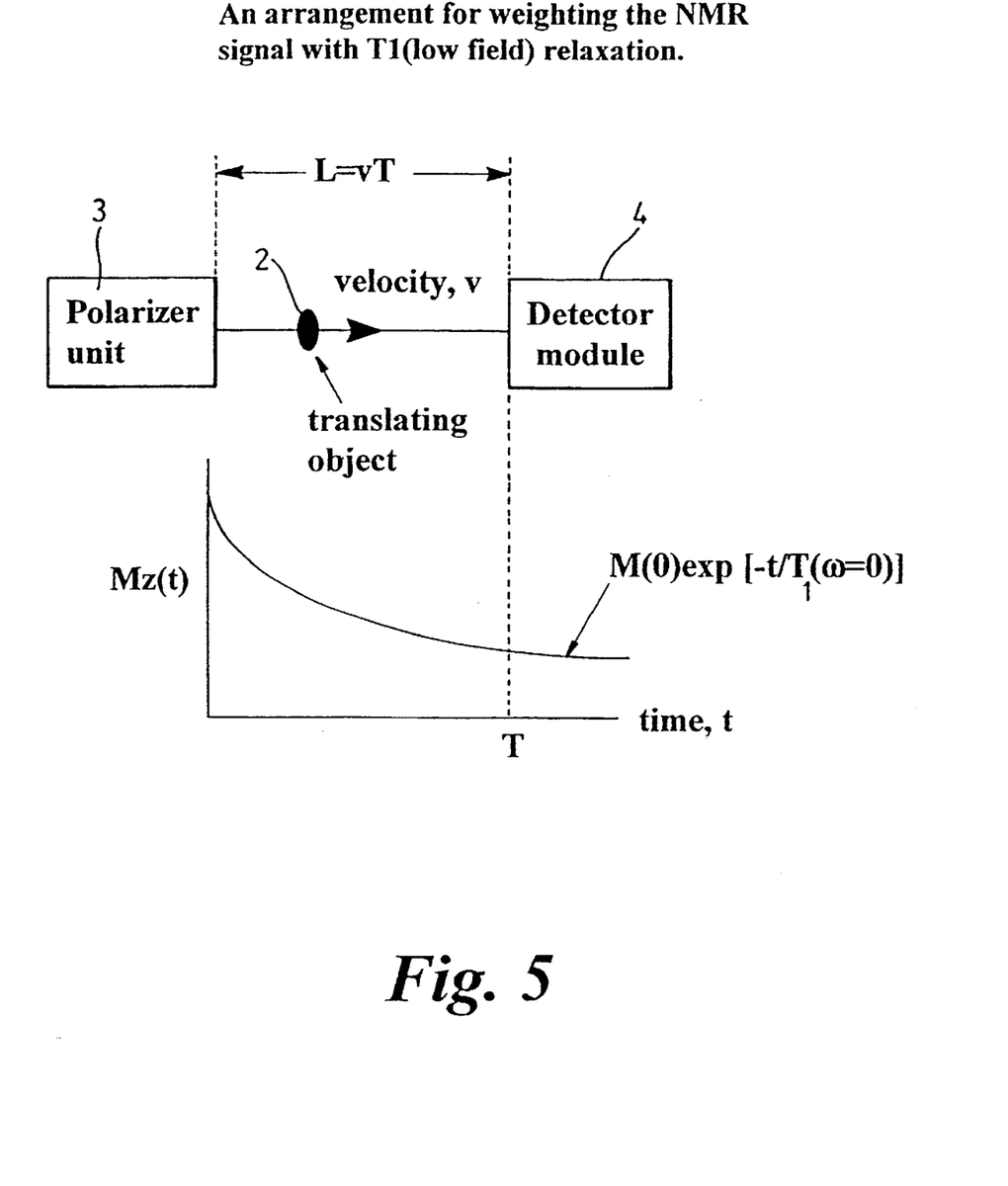
FIG. 5 shows an arrangement for weighting motional echoes with $T_1$ (low field) relaxation according to the present invention.
Figure 6:
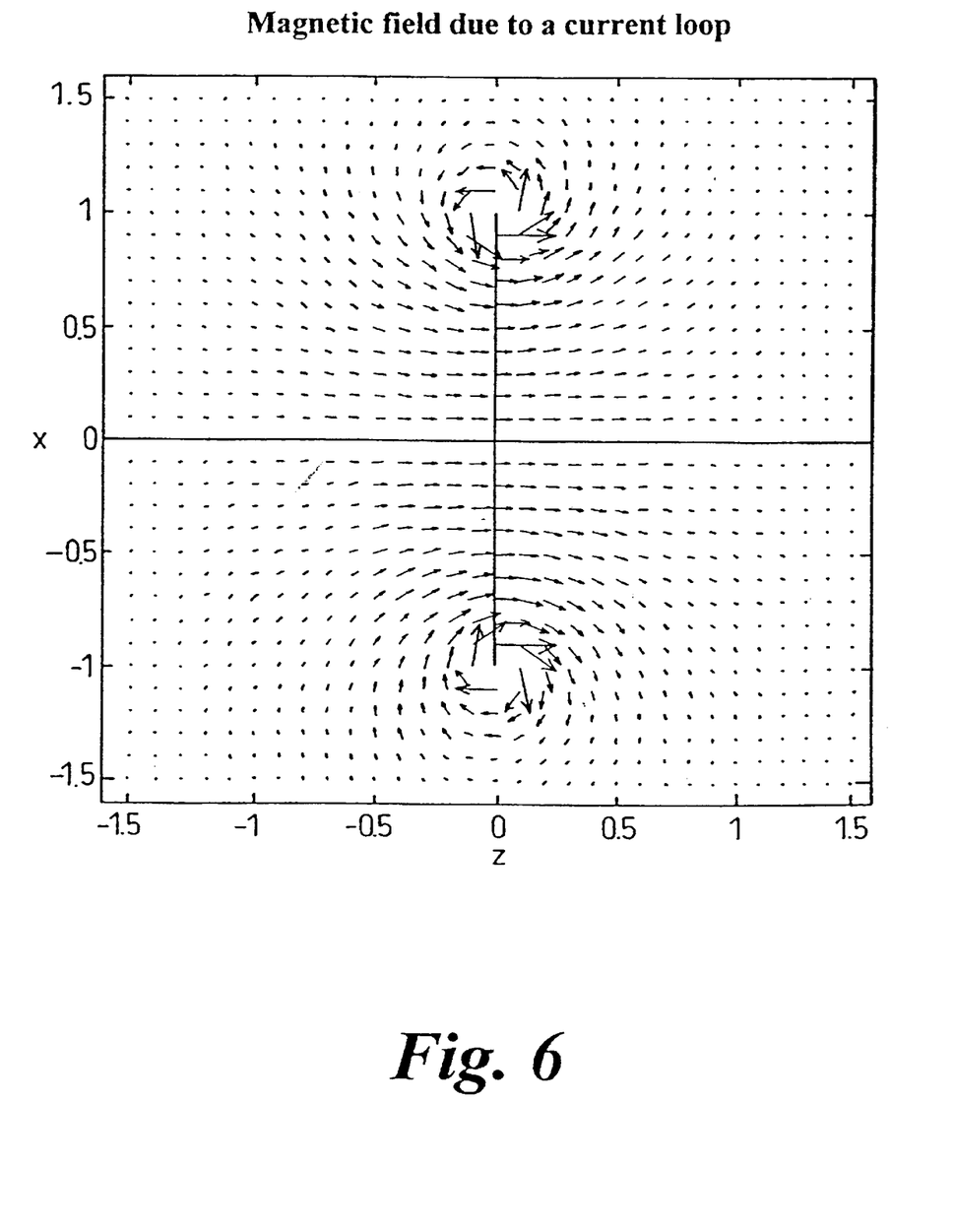
FIG. 6 shows a simulation of the magnetic field direction and strength as a function of x and z spatial co-ordinates for a $G_x$ unit.
Figure 7:
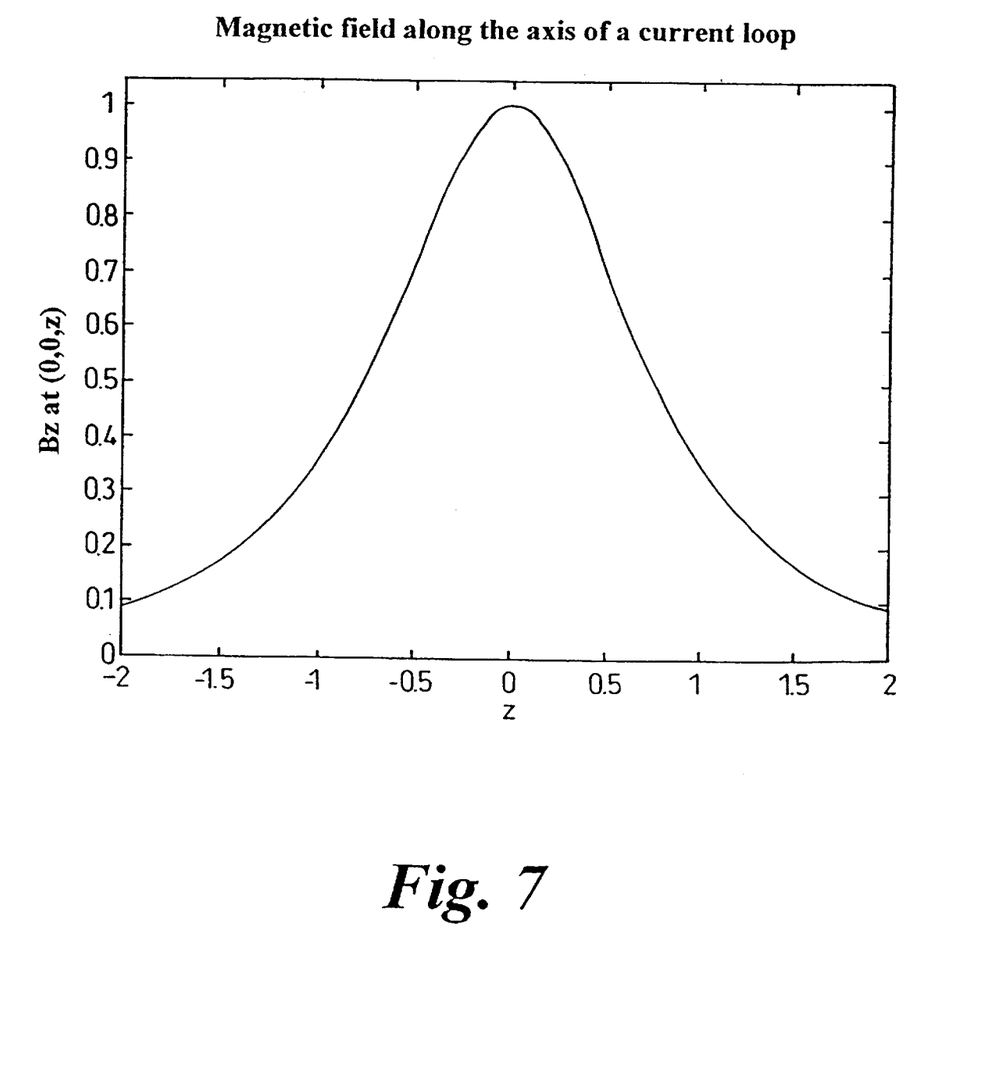
FIG. 7 shows a simulation of the magnetic field strength $B_z$ along the axis of a current loop as a function of z, at x=0, for the $G_x$ unit of FIG. 6.
Figure 8:
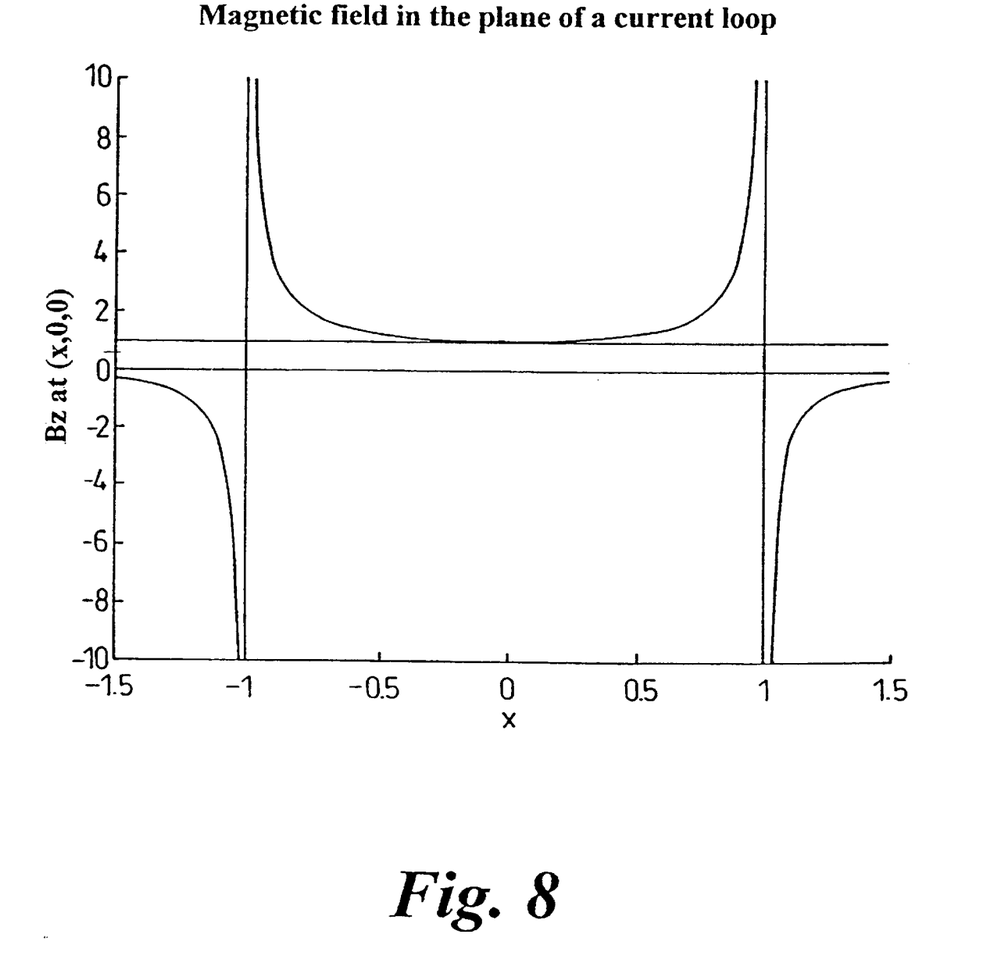
FIG. 8 shows a stimulation of the magnetic field strength $B_z$ in the plane of a current loop as a function of x, at z=0, for the $G_x$ unit of FIG. 6.
Figure 9:
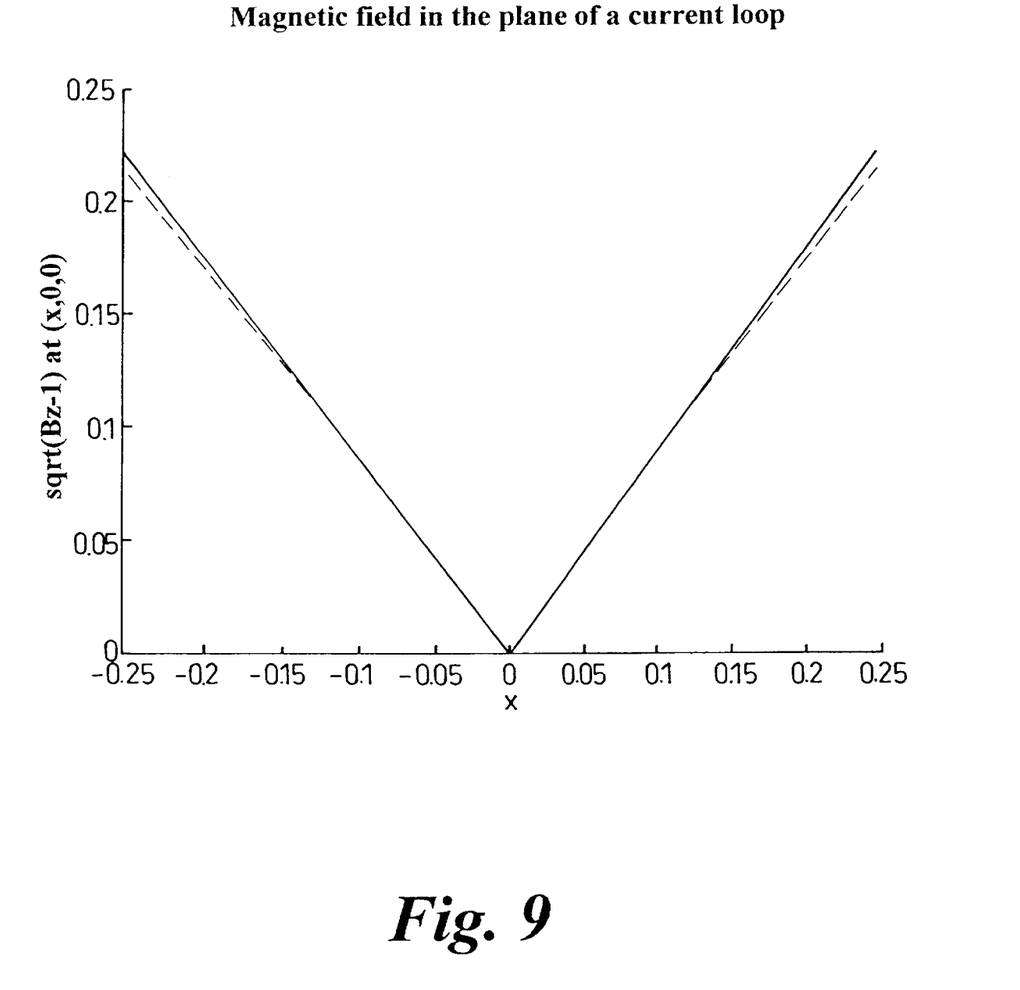
FIG. 9 shows a simulation of the square root of magnetic field strength $B_z$-1 in the plane of a current loop as a function of x, at z=0, for the $G_x$ unit of FIG. 6.

Between the polarizer unit 3 and the detector module 4, the objects 2 being analysed contain longitudinal magnetization relaxing in the earth's magnetic field. By varying the length of time spent between the polarizer 3 and detector module 4, various amounts of $T_1$ (low field) relaxation can be introduced. A suitable arrangement is shown in FIG. 5. As shown, the degree of residual magnetization at time t is given by the expression $M_z(t)=M(0) \exp[-t/T_1(\omega=0)]$, where M(0) is the initial magnetization induced by the polarizer unit 3. The time t between the object leaving the polarizer unit 3 and arriving at the detector module 4 is, of course, determined by the length L=vT.

Diffusion Weighting in the Spectrum

Diffusion weighting can be created, explicifly, using two or more $G_x$ units. Each $G_x$ unit creates a constant, localized, non-uniform gradient, $G_x$ across the solenoid axis and transverse to the $B_0$ field. Motion of the object through these static $G_x$ gradients is equivalent to imposing time-varying (pulsed) field gradients. The standard pulsed gradient spin echo or stimulated echo pulse sequences can then be used to weight the spectrum, which is obtained by Fourier transforming the spin echo or stimulated echo.

3) On-line Compositional Analysis in a Moving Object by Difference Spectroscopy Using Spin and/or Stimulated Echoes In some applications the acquisition of a single, parameter-weighted spectrum is insufficient to determine the chemical composition. In such cases it may be necessary to take the difference between a spectrum (called the first spectrum) acquired with an attenuation weighting which is insensitive to the presence of a particular component and a second spectrum weighted with a parameter (such as $T_2^*$, $T_2$, $T_1$, or D) which is more sensitive to the presence of the chemical component. Taking suitably processed differences between the first and second spectra can then be used to determine the amount of the component in the food.

The first spectrum can be calculated from the FID generated by the first 90° pulse in the pulse sequences listed above. The second spectrum can be calculated from one (or more) of the spin echoes or stimulated echoes generated subsequently.

The difference protocol may, if necessary, be combined with spectrum registration software and/or signal processing software, such as Wiener filtering. All such operations can be performed in the least possible time using a fast computer, such as a 233 MHz PC.

B) The Time Domain

In some applications, it is not necessary to Fourier transform the time domain signal. For example, conventional solid/liquid ratios can be determined from the free induction decay in the time domain. Similarly, an on-line determination of emulsion droplet size distribution from the diffusion weighted stimulated echo is also possible. These protocols are standard techniques in off-line NMR analysis, but it has been recognized that these can also be applied in the on-line mode with the hardware described previously.

The present invention has thus far been described with reference to specific embodiments. It will be understood, however, that a number of modifications can be made thereto. For example, although the preferred embodiment requires that an object is undergoing continuous, uniform translational motion, in fact the object can be undergoing any non-zero velocity or finite acceleration.

This has particular significance where objects to be analysed are falling off the end of a conveyor belt, for example. In that situation, the motion of an object can be precisely characterised where it is undergoing continuous acceleration. Arrival of the object into the NMR system and/or determination of its translational motion can be determined by optical beams, as discussed earlier.

SPECIFIC EXAMPLES

A number of examples of commercial applications of the on-line NMR spectrometer described above are now given. This list is purely illustrative and far from exhaustive.

Example 1

Analysis of fat/water ratios. At a proton resonance frequency of 20 MHz, a chemical shift of 3 ppm (corresponding, approximately, to the chemical shift difference between lipid CH protons and water) is equivalent to 60 Hz, so provided the $B_0$ field is sufficiently homogeneous to give linewidths of less than 60 Hz, separate fat and water peaks are normally resolvable. Even if they are not resolvable, either the fat or water signals can often be eliminated by the $T_1$-null method using the inversion recovery sequence or by use of $T_2$ weighting created with a Hahn echo and a pulse spacing chosen to reduce or eliminate one or other of the chemical components. The signal intensity can then be used as an on-line monitor of the fat/water ratio.

Example 2

On-line monitoring of protein/polysaccharide/water/sugar/lipid composition of food materials.

Example 3

On-line detection of the degree of ripeness of fruit, especially if ripening is associated with changes of chemical composition, such as increased sugar content (sweetness) and reduced starch content (softening of the texture).

Example 4

On-line monitoring of the particle sizes in powders. Different particle sizes are associated with different susceptibility gradients and hence different $T_2^*$ values. This causes differing spectral broadening.

Example 5

On-line monitoring of the composition of flowing chemical mixtures in the chemical and pharmaceutical industries.

Example 6

On-line measurements of solid/liquid ratios from the free induction decay.

Example 7

On-line measurements of droplet size distributions in emulsions.

Appendix 1

Calculation of the Field Gradients Created by a Single Current Loop (the $G_x$ unit)

A MATLAB program has been written to calculate the magnetic field due to a circular current loop or coil centred at the origin in the xy-plane. This comprises "the $G_x$ unit". The results are shown in FIGS. 6 to 9. Note the non-linear $G_x$ and $G_z$ gradients created by this unit.

Appendix 2

Example Methodology for Compositional Analysis Using a Poorly Resolved On-line NMR Spectrum Here we show how it is, in principle, possible to analyze a mixture of chemical species using a poorly resolved on-line, low-field NMR spectrum such as that illustrated in FIG. 4.

1. Consider a mixture of N chemical species, each species being labelled by the subscript, i, such that i=1, 2 ... N.

2. We assume that each chemical species is characterized by an NMR spectrum, $I_i(\omega)$, where $\omega$ is the NMR observation frequency. $I_i(\omega)$ can be measured for each pure chemical species in the on-line NMR spectrometer described in this patent. $I_i(\omega)$ would typically be a Lorentzian or Gaussian spectral lineshape, but this is not a necessary assumption.

3. We further assume, for illustrative simplicity, that the functional form of $I_i(\omega)$ does not depend on the presence of other species, j, not the same as i. In other words, we assume simple additivity of component spectra in the mixture.

4. The overall NMR spectrum, $S(\omega)$, observed for a mixture of N species is then the simple sum of the component spectra:

$$S(\omega)=\Sigma_i x_i I_i(\omega) \quad i=1,2 \ldots N. \epsilon \Sigma_i x_i=1.$$

To analyze the mixture composition, $X_1, X_2, \ldots X_N$, we need only measure $S(\omega)$ at N different frequencies, $\omega_j$ for $j=1,2 \ldots N$. Then $$S(\omega_j)=\Sigma_i x_i I_i(\omega_j)$$

This can be written in matrix form:

$$S=I.x \text{ where } I_{ij} \text{ is the matrix element, } I_j(\omega_j)$$

The mixture composition is then obtained by simple matrix solution:

$$x=I^{-1}.S$$

This shows that in order to analyze the mixture composition from a poorly resolved NMR spectrum it is only necessary to measure the intrinsic coefficients $I_{ij}$. This can be done by measuring the spectrum, $I_i(\omega)$, for a known amount of each pure species, i, under identical NMR spectrometer conditions.

The assumption of simple additivity can be removed at the expense of increased complexity, and requires additional calibration of interacting mixtures. A typical analytical method where there is non-additivity would be that of Principle Component Analysis as described, for example, in the book, "Factor Analysis in Chemistry", 2$^{nd}$ Edition, John Wiley and Sons, by E. R. Malinowski.

What is claimed is:

1. A method of nuclear magnetic resonance spectroscopy comprising the steps of:

conveying an object to be analysed through an NMR module at a redetermined velocity, v;

generating, within the NMR module, a spatially characterised, constant magnetic field $B_0$ substantially parallel to the direction of the velocity, v;

generating, within the NMR module, a radiofrequency field $B_1$ pulse transverse to field $B_0$ using a coil having cylindrical geometry whose cylinder axis is aligned along the direction of velocity, by using a first series of loops in said coil in which the plane of each loop is tilted with respect to the cylinder axis to generate a field with a component perpendicular to the cylinder axis, and using a second series of loops in said coil which eliminate a longitudinal component of the RF field generated by said first series of loops;

providing a sufficient continuous length of RF coil according to the velocity, v of objects passing therethrough in order to enable the step of detecting nuclear magnetic resonance signals weighted with at least one selected nuclear magnetic resonance parameter from said object while said object is moving at said predetermined velocity.

2. The method according to claim 1 wherein said detecting step comprises detecting a free induction decay signal from the object passing through the NMR module.

3. The method according to claim 1 wherein said detecting step comprises detecting the spin echo or stimulated echo of the object passing through the NMR module.

4. The method according to any one of claims 1 to 3 in which the spatially characterised constant magnetic field $B_0$ is substantially spatially uniform.

5. The method according to any one of claims 1 to 3 further including the step of providing said $B_0$ and $B_1$ fields as spatially homogeneous fields over a module length, in the direction of v, of at least $L_{min}=\int_0^{AQ} dt \, v(t)$, where AQ is the data acquisition time required to determine the magnetic resonance measurements and v(t) is the instantaneous velocity.

6. The method according to claim 1 wherein the step of generating the radiofrequency field pulse $B_1$ includes the step of triggering a first pulse with reference to arrival of the object in the module.

7. The method according to claim 6 further including the step of determining the timing of successive RF pulses $B_1$ according to a real time determination of the object velocity v.

8. The method according to claim 1 further including the step of inducing a longitudinal magnetisation in the object parallel or antiparallel to its direction of movement prior to its entry into the NMR module.

9. The method according to claim 8 in which the step of inducing longitudinal magnetisation in the object comprises the step of passing the object through a polarizing module, for a predetermined time period, the polarizing module providing a magnetic field parallel to the direction of movement of the object.

10. The method according to claim 9 in which the predetermined time period is at least $5 \times T_1$, where $T_1$ is the longitudinal relaxation time.

11. The method according to claim 1 further including the step of substantially preventing rotational movement of the object.

12. The method according to claim 1 further including the step of substantially preventing movement of the object in any direction transverse to the predetermined velocity, v.

13. The method according to claim 1 in which the object is an element of a fluid being conveyed through the NMR module.

14. The method according to claim 1 further including the step of generating a chemical shift resolved spectrum by performing a Fourier transform on a free induction decay signal, a spin echo signal or a stimulated echo signal.

15. The method according to claim 1 further including the step of generating a chemical spectrum of the conveyed object from an acquired free induction decay signal, and weighting said spectrum with a further nuclear magnetic resonance parameter.

16. The method according to claim 15 wherein said further parameter is one or more of $T_2^*$, $T_2$, $T_1$, $T_{ip}$, D, or magnetization transfer rate, where $T_2^*$ is the transverse spin dephasing time; $T_2$ is the transverse relaxation time; $T_1$ is the longitudinal relaxation time; and D is the self-diffusion coefficient.

17. The method of claim 16 wherein said further parameter is $T_1$ and wherein said RF pulse generating step includes inversion of the polarized magnetisation of the object by said $B_0$ field by a hard 180° pulse followed by recovery for a predetermined time, $t_1$, prior to said transverse RF pulse.

18. The method of claim 9 further including the step of generating a chemical spectrum of the conveyed object from an acquired free induction decay signal, and weighting said signal with a further nuclear magnetic resonance parameter, $T_1$, and wherein a predetermined amount of $T_1$ relaxation is introduced by varying a time delay between the conveyed object leaving said polarizer module and entering said NMR module.

19. The method of claim 16 wherein said further parameter is D, further including the step of generating, within the NMR module, a spatially localised, non-uniform magnetic field gradient $G_x$ substantially transverse to $B_0$.

20. The method of claim 16 wherein said further parameter is $T_2$, wherein said RF pulse generating step includes generating a series of hard 180° pulses in a Hahn echo, or Carr Purcell Meiboom Gill pulse sequence.

21. The method of claim 16 wherein said further parameter is $T_2^*$, wherein said RF pulse generating step comprises a single 90° pulse.

22. The method of claim 1 further including the step of conveying a series of discrete objects to be analysed through said NMR module at predetermined intervals.

23. Apparatus for gathering spectroscopic nuclear magnetic resonance data comprising:

- a first field generating means for generating a spatially characterised, constant magnetic field $B_0$ in an NMR module volume having a predetermined length along a longitudinal axis thereof, the $B_0$ field being parallel to said longitudinal axis;
- a second field generating means for generating, within the NMR module volume, radiofrequency field $B_1$ pulses transverse to field $B_0$, the second field generating means comprising a coil having cylindrical geometry whose cylinder axis is aligned along the direction of velocity, the coil including a first series of loops in which the plane of each loop is tilted with respect to the cylinder axis so as to generate a field with a component perpendicular to the cylinder axis, and a second series of loops which generate a field which eliminates a longitudinal component of the RF field generated by said first series of loops;
- means for conveying a series of objects at a predetermined velocity through the first and second field generating means;
- receiver means for detecting nuclear magnetic resonance signals weighted with at least one selected nuclear magnetic resonance parameter from said object while said object is moving at said predetermined velocity.

24. Apparatus according to claim 23 in which said first and second field generating means each have a cylindrical geometry coaxial with one another.

25. Apparatus according to claim 23 or 24 in which said first field generating means comprises a hollow cylindrical permanent magnet.

26. The apparatus of claim 23 further including means for generating a chemical shift resolved spectrum of the conveyed object within the NMR module.

* * * * *